United States Patent [19]

Preissman

[11] Patent Number: 5,449,361
[45] Date of Patent: Sep. 12, 1995

[54] ORTHOPEDIC CABLE TENSIONER

[75] Inventor: Howard E. Preissman, Dallas, Tex.

[73] Assignee: AMEI Technologies Inc., Wilmington, Del.

[21] Appl. No.: 52,058

[22] Filed: Apr. 21, 1993

[51] Int. Cl.⁶ .............................................. A61B 17/56
[52] U.S. Cl. ................................... 606/103; 606/61; 606/74; 140/123.5
[58] Field of Search ................... 606/144, 139, 1, 103, 606/61, 74; 140/123.5

[56] References Cited

U.S. PATENT DOCUMENTS

| | | |
|---|---|---|
| 409,721 | 8/1889 | Williams, Jr. |
| 1,258,580 | 3/1918 | Lassiter. |
| 1,304,620 | 5/1919 | Steinkoenig. |
| 1,346,940 | 7/1920 | Collins. |
| 1,347,579 | 7/1920 | Henrikson. |
| 1,388,716 | 8/1921 | Hughes. |
| 1,641,077 | 8/1927 | Fouquet. |
| 1,717,766 | 6/1929 | Eimler. |
| 2,049,361 | 7/1936 | Ericsson. |
| 2,279,068 | 4/1942 | Sierbrandt ........................ 140/121 |
| 2,291,413 | 7/1942 | Sierbrandt. |
| 2,455,609 | 12/1948 | Scheib. |
| 2,509,290 | 5/1950 | Elvin et al. |
| 2,883,096 | 4/1959 | Dawson ........................... 223/102 |
| 2,928,395 | 3/1960 | Forbes et al. |
| 3,035,476 | 5/1962 | Fogden ............................ 87/9 |
| 3,035,583 | 5/1962 | Hirsch et al. |
| 3,078,755 | 2/1963 | Chace, Jr. ........................ 87/9 |
| 3,111,945 | 11/1963 | Von Solbrig. |
| 3,215,768 | 11/1965 | Murphy ........................... 174/36 |
| 3,233,800 | 2/1966 | Catania ........................... 223/102 |
| 3,323,208 | 6/1967 | Hurley, Jr. ....................... 30/124 |
| 3,507,270 | 4/1970 | Ferrier. |
| 3,587,585 | 6/1971 | Ceravolo. |
| 3,762,418 | 10/1973 | Wasson. |
| 3,802,438 | 4/1974 | Wolvek. |
| 3,892,241 | 7/1975 | Leveen. |
| 3,910,281 | 10/1975 | Kletschka et al. |
| 3,952,377 | 4/1976 | Morell ............................. 24/136 |
| 3,965,541 | 6/1976 | Davison ........................... 24/115 |
| 3,976,079 | 8/1976 | Samuels et al. |
| 3,993,109 | 11/1976 | Fortsch ........................... 140/123.6 |
| 4,050,464 | 9/1977 | Hall. |
| 4,084,625 | 4/1978 | Brinegar .......................... 140/123.5 |
| 4,128,100 | 12/1978 | Wendorff. |
| 4,200,126 | 4/1980 | Fish. |
| 4,283,933 | 8/1981 | Wiener ............................ 72/409 |
| 4,291,698 | 9/1981 | Fuch et al. |

(List continued on next page.)

FOREIGN PATENT DOCUMENTS

| | | |
|---|---|---|
| 218602 | 9/1956 | Australia. |
| 1158422 | 12/1983 | Canada. |
| 0019062A1 | 11/1980 | European Pat. Off. |
| 0117981 | 9/1984 | European Pat. Off. |
| 999646 | 5/1964 | France. |
| 1177769 | 9/1964 | Germany. |
| 1958429 | 7/1971 | Germany. |
| 3146634 | 6/1983 | Germany. |

(List continued on next page.)

*Primary Examiner*—Tamara L. Graysay
*Attorney, Agent, or Firm*—Baker & Botts

[57] ABSTRACT

Apparatus and methods are provided to allow attachment of one or more surgical cables in the form of a loop to selected portions of a patient's body. The apparatus includes a cable tensioner which applies manual force to the surgical cable at a one to one ratio during installation. The cable tensioner includes a first handle fixed to one end of an elongated shaft and a second handle which is slidably disposed on the exterior of the elongated shaft. The second handle may include a unidirectional paw to allow movement of the second handle in only one direction towards the fixed handle. During the installation of two or more surgical cables, a tensioner may be engaged with each cable to allow the surgeon to alternately tighten and/or loosen the associated cable as required to provide the optimum mechanical support for the bones or other portions of the patient's body which are engaged by the respective surgical cable loops. The elongated shaft may be modified to accommodate the use of various crimps and locks to securely engage a loop in the cable after the desired tension has been placed on the surgical cable.

17 Claims, 3 Drawing Sheets

U.S. PATENT DOCUMENTS

| | | | |
|---|---|---|---|
| 4,333,649 | 6/1982 | Vaughn et al. | 273/73 |
| 4,387,489 | 6/1983 | Dudek | 24/133 |
| 4,412,474 | 11/1983 | Hara | 87/6 |
| 4,509,233 | 4/1985 | Shaw | 24/136 |
| 4,527,554 | 7/1985 | Klein . | |
| 4,570,618 | 2/1986 | Wu . | |
| 4,587,963 | 5/1986 | Leibinger et al. . | |
| 4,592,355 | 6/1986 | Antebi | 606/144 |
| 4,623,717 | 12/1986 | Covitz . | |
| 4,643,178 | 2/1987 | Nastari et al. . | |
| 4,712,770 | 12/1987 | Wiederkehr | 254/98 |
| 4,716,886 | 1/1988 | Schulman et al. . | |
| 4,741,330 | 5/1988 | Hayhurst . | |
| 4,750,492 | 6/1988 | Jacobs . | |
| 4,773,402 | 9/1988 | Asher et al. . | |
| 4,790,303 | 12/1988 | Steffee . | |
| 4,889,110 | 12/1989 | Galline et al. | 606/69 |
| 4,901,721 | 2/1990 | Hakki | 606/103 |
| 4,946,462 | 8/1990 | Watanabe | 606/148 |
| 4,966,600 | 10/1990 | Songer et al. | 606/74 |
| 4,969,895 | 11/1990 | McLeod et al. | 606/96 |
| 5,052,094 | 10/1991 | Plasse et al. | 29/252 |
| 5,057,113 | 10/1991 | Mingozzi | 606/103 |
| 5,059,207 | 10/1991 | Shah | 606/223 |
| 5,089,012 | 2/1992 | Prou | 606/224 |
| 5,092,868 | 3/1992 | Mehdian | 606/74 |
| 5,116,340 | 5/1992 | Songer et al. | 606/103 |
| 5,127,144 | 7/1992 | Plasse et al. | 29/252 |
| 5,137,738 | 7/1992 | Korthoff et al. | 606/224 |
| 5,199,146 | 4/1993 | Grover et al. | 29/268 |
| 5,312,410 | 5/1994 | Miller et al. | 606/86 |

FOREIGN PATENT DOCUMENTS

| | | | |
|---|---|---|---|
| 123046 | 10/1926 | Switzerland . | |
| 275268 | 8/1951 | Switzerland . | |
| 163340 | 6/1921 | United Kingdom | 24/136 R |
| 579288 | 7/1946 | United Kingdom | 140/123.5 |
| 958284 | 5/1964 | United Kingdom . | |
| 506401 | 5/1976 | U.S.S.R. . | |

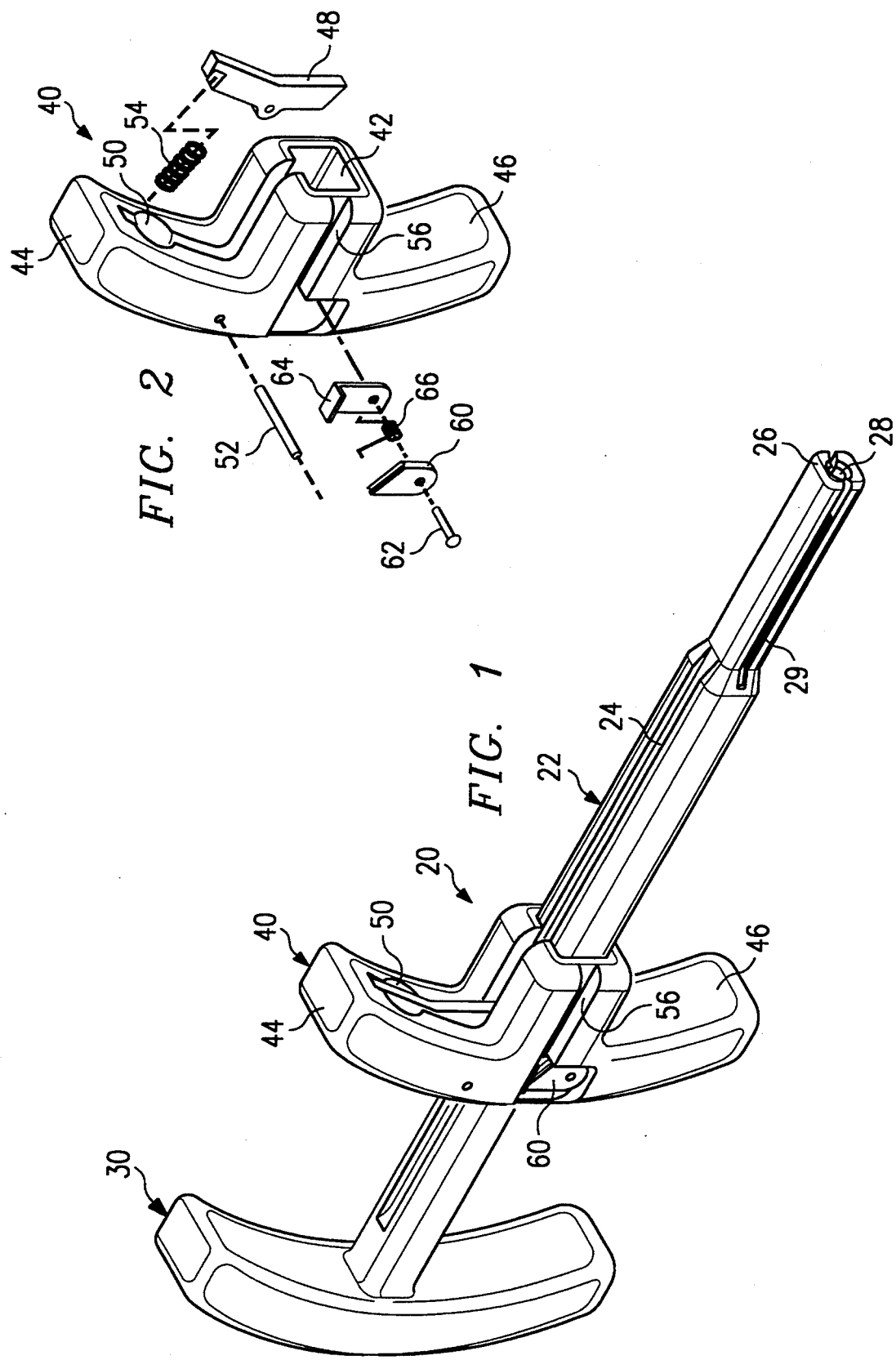

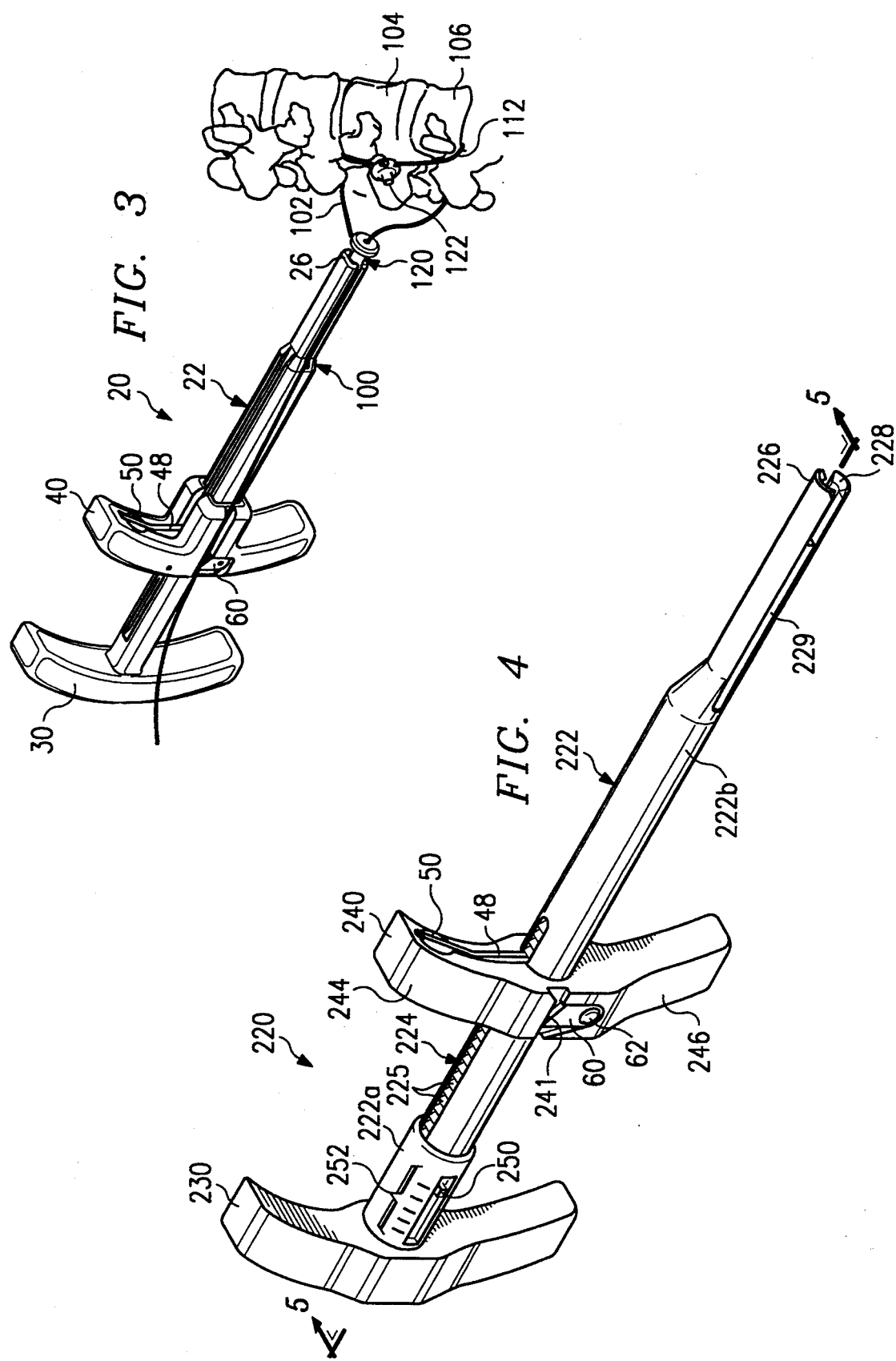

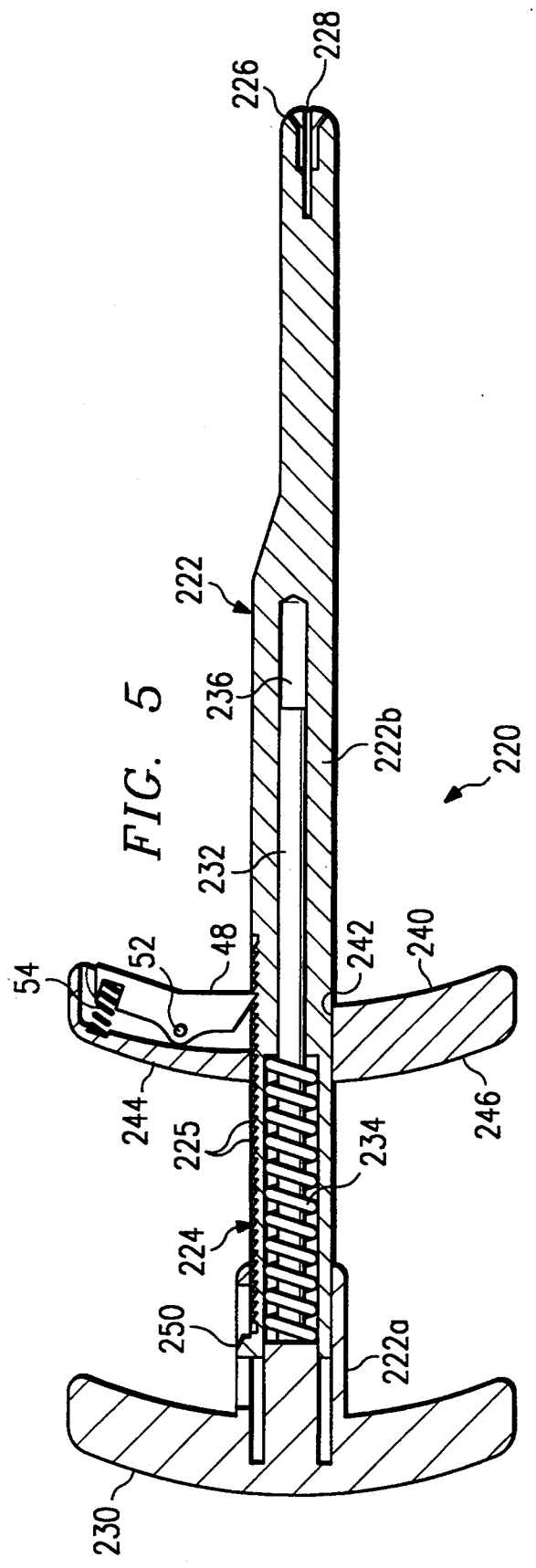
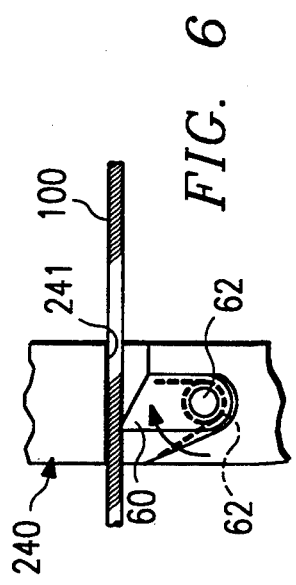

ORTHOPEDIC CABLE TENSIONER

RELATED APPLICATION

This application is related to copending U.S. patent application Ser. No. 08/052,191 filed Apr. 21, 1993, entitled Surgical Cable Leader and Terminations, pending; application Ser. No. 08/253,200 filed Jun. 1, 1994, entitled Surgical Cable Crimp pending, which is a continuation of U.S. patent application Ser. No. 08/052,059 filed Apr. 21, 1993, entitled Surgical Cable Crimp, now abandoned; and application Ser. No. 08/230,196 filed Apr. 20, 1994, entitled Surgical Cable and Cable Crimp, pending, which is a continuation of U.S. patent application Ser. No. 08/051,179 filed Apr. 21, 1993, entitled Surgical Cable and Cable Crimp now abandoned.

TECHNICAL FIELD OF THE INVENTION

This invention relates to surgically implanted wires and cables and more particularly relates to improved methods and apparatus for use in surgically installing wires and cables at selected locations in a patient's body.

BACKGROUND OF THE INVENTION

Surgical wires and cables are used in a variety of medical procedures, for example reconstructive spine surgery such as fusions, spine trauma surgery, total hip arthroplasty, fracture fixation, open heart surgery for closure of the sternum, oral/facial surgery to fix mandibular fractures and other trauma surgery. Often, surgical cables and wires are used to encircle bones to hold them together for healing if broken or for fusion in the case of some types of spinal surgery. For purposes of this application, "cable" includes monofilament and single strand wire along with multifilament and multistrand cable and wire ropes.

Problems sometimes occur with placing the correct tension in surgical cables during installation. Current systems for attaching surgical cables to selected portions of a patient's body have experienced problems with the cables being applied too tightly and creating a vascular necrosis of the bone around which the cables are wrapped. At the same time, surgical cables must be tight enough to achieve the desired mechanical fixation. Many conventional systems are difficult to manipulate and surgeons have experienced problems in properly positioning the cable while at the same time applying the desired tension. Many currently available products do not provide direct feedback to the surgeon concerning the amount of tension being applied to the cable. The mechanical advantage incorporated into current products effectively blocks tactile sensing and control of the amount of applied tension.

Examples of apparatus and equipment used to install cables and wires during surgical and other medical procedures are shown in U.S. Pat. No. 4,050,464 entitled "Surgical Cable Tensioning Instrument"; U.S. Pat. No. 4,587,693 entitled "Instrument for Positioning a Cerclage Fixation Device Around Fractured Bone Parts"; U.S. Pat. No. 4,966,600 entitled "Surgical Severance Method"; and U.S. Pat. No. 5,057,113 entitled "Device for Tensioning Traction Wires in Orthopedic Surgery". The above-referenced patents are incorporated by reference for all purposes within this Application.

SUMMARY OF THE INVENTION

In accordance with the present invention, disadvantages and problems associated with previous systems and methods for installing surgical cables with selected portions of a patient's body have been substantially reduced or eliminated.

The present invention includes improved methods and apparatus for use with surgical cables in a wide variety of surgical and medical procedures. A cable tensioner incorporating the present invention allows a surgeon to apply tension to a surgical cable loop around a bone or bones and to avoid applying excess tension. The cable tensioner can be easily inserted into a surgical incision to apply tension at hard-to-reach locations such as spinal vertebrae.

An important technical advantage of the present invention includes providing tactile feedback to a surgeon using a cable tensioner incorporating the present invention with a 1:1 ratio of force applied to the cable tensioner and tension applied to the attached surgical cable. The cable tensioner provides a grip for holding the surgical cable without undue interference and allows direct tactile sensing and control of the tension applied to the surgical cable.

A cable tensioner incorporating the present invention includes a fixed handle on one end of the tensioner and a second handle which may slide longitudinally towards the first handle. This feature allows the physician to incrementally tighten a surgical cable attached to the tensioner. The feature is extremely beneficial when more than one cable is to be installed. It is often important for the physician to incrementally tighten cables at different positions on a medical or surgical construct, such as a HARRINGTON rod, until all cables are sufficiently secured. If the physician needs to loosen a particular cable, this may be accomplished by releasing a unidirectional pawl carried by the slidable handle.

Another technical advantage of the present invention results from providing a relatively low cost cable tensioner which may be discarded after each use. Alternatively the present invention may be used to provide a cable tensioner which can be reused for multiple surgical procedures.

A further technical advantage of the present invention includes providing a cable tensioner with a gauge which indicates the amount of force applied by the cable tensioner to a surgical cable attached to the tensioner.

BRIEF DESCRIPTION OF THE DRAWINGS

For a more complete understanding of the present invention and the advantages thereof, reference is now made to the following description taken in conjunction with the accompanying drawings in which:

FIG. 1 is an isometric drawing showing a cable tensioner incorporating the present invention;

FIG. 2 is an isometric drawing with portions exploded away showing the second, slidable handle used with the tensioner of FIG. 1;

FIG. 3 is an isometric sketch showing the cable tensioner of FIG. 1 used to secure surgical cable loops with selected vertebrae in a patients' spine;

FIG. 4 is an isometric drawing of a cable tensioner incorporating an alternative embodiment of the present invention;

FIG. 5 is a drawing in section and in elevation with portions broken away taken along line 5—5 of FIG. 4; and FIG. 6 is a schematic representation showing a surgical cable engaged with the second, slidable handle of the tensioner shown in FIGS. 4 and 5.

DETAILED DESCRIPTION OF THE INVENTION

The preferred embodiments of the present invention and its advantages are best understood by referring to FIGS. 1 through 6 of the drawings, like numerals being used for like and corresponding parts of the various drawings.

Cable tensioner 20 incorporating the present invention is shown in FIGS. 1 and 3. Cable tensioner 20 is preferably used with a surgical cable and a crimp to trap the desired amount of tension in a loop formed by the surgical cable and crimp. Surgical cable 100, crimp 120 and first loop 102 are shown in FIG. 3 as examples which may be used with cable tensioner 20. The use of cable tensioner 20 to install surgical cable 100 to selected portions of a patient's body and to trap the desired amount of tension within loop 102 using crimp 120 will be described later in more detail.

Cable tensioner 20 has three main components, elongated shaft 22, first handle 30 and second handle 40. An important feature of the present invention is that the main components of cable tensioner 20 may be formed from molded plastic. Thus, cable tensioner 20 is relatively inexpensive and may be discarded after only one use in a surgical procedure. This advantage of the present invention is particularly important due to the increased concern with sterilization of surgical instruments to prevent the spread of AIDS and other diseases.

First handle 30 is preferably secured to one end of elongated shaft 22. First handle (sometimes referred to as "fixed handle") 30 is generally configured to fit within the palm of a surgeon's hand (not shown). Elongated shaft 22 and first handle 30 cooperate to form a generally "T" shaped surgical tool.

Second handle 40 is slidably disposed on the exterior of elongated shaft 22 intermediate the ends thereof. Elongated shaft 22 has a generally rectangular cross section. First slot 24 is formed in the exterior of elongated shaft 22 intermediate the ends thereof. Second handle 40 includes opening 42 which is sized to fit over the portion of elongated shaft 22 containing first slot 24. Opening 42 cooperates with the exterior of elongated shaft 22 to allow second handle 40 to slide longitudinally over the exterior of elongated shaft 22.

The other end 26 of elongated shaft 22 has an opening 28 which provides a portion of the means for releasably securing a portion of a surgical cable with end 26 of elongated shaft 22. A second slot 29 is provided in the exterior of elongated shaft 22 adjacent to and extending from end 26. As will be explained later in more detail, second slot 29 is provided to assist with attachment of a surgical cable to second handle 40.

Second handle 40 and elongated shaft 22 also define a generally "T" shaped configuration. Second handle (sometimes referred to as "slidable handle") 40 preferably includes extensions 44 and 46 which are provided for engagement by the fingers of a surgeon's hand. Cable tensioner 20 is frequently used by resting first, fixed handle 30 against the palm of a surgeon's hands and engaging extensions 44 and 46 by the fingers of the surgeon's hand. When the surgeon squeezes her fingers, second handle 40 will slide longitudinally towards first, fixed handle 30. This movement provides a direct tactile feedback with a 1:1 ratio between force applied to second handle 40 and tension applied to a surgical cable attached to tensioner 20.

Second handle 40 includes pawl 48 which is disposed within recess 50 of extension 44. Pin 52 is provided to secure pawl 48 within recess 50 and to allow pawl 48 to pivot with respect to pin 52 and the exterior of elongated shaft 22 adjacent thereto. First spring 54 is disposed within recess 50 and contacts a portion of pawl 48. Spring 54 cooperates with pivot pin 52 to bias pawl 48 to contact the exterior of elongated shaft 22 adjacent thereto. Therefore, pawl 48 will normally ride against the exterior of elongated shaft 22 and prevent movement of second handle 40 away from first handle 30.

Pawl 48 is preferably sized to fit within longitudinal slot 24 and to engage elongated shaft 22 therein. Spring 54 and pivot pin 52 cooperate with pawl 48 to allow longitudinal movement of second handle 40 towards first handle 30. In a similar manner spring 54, pivot pin 52 and pawl 48 cooperate with each other to prevent undesired movement of second handle 40 in the direction away from first handle 30.

Second handle 40 includes cleat 60 which is attached to the exterior of second handle 40 by pivot pin 62. Since second handle 40 is preferably formed from molded plastic, plate 64 is disposed between cleat 60 and the adjacent portions of second handle 40. Torsion spring 66 is provided to bias cleat 60 into contact with plate 64. As will be explained later in more detail, cleat 60 cooperates with plate 64 to trap a portion of surgical cable 100 therebetween.

As shown in FIG. 3 cable tensioner 20 may be used with surgical cable 100 to secure first loop 102 with selected portions of a patient's body such as vertebrae 104 and 106. Crimp 120 is preferably secured to one end of surgical cable 100 and loop 102 placed around the selected portion of the patent's body. Crimp 120 and the one end of surgical cable 100 are then secured to end 26 of elongated shaft 22 opposite from first handle 30° A portion of surgical cable 100 is placed within second longitudinal slot 29 in the exterior of elongated shaft 22 and slot 56 in second handle 40 adjacent to cleat 60. Second slot 29 in elongated shaft 22 and slot 56 in handle 40 cooperate with each other to align surgical cable 100 with elongated shaft 22 and to allow engagement of a portion of surgical cable 100 with cleat 60.

Cleat 60, torsion spring 66 and pivot pin 62 cooperate with each other to secure surgical cable 100 to second handle 40. If desired, cleat 60 could be replaced by other mechanisms for trapping surgical cable 100 with second handle 40. An example would be one or more set screws or locking nuts carried by second handle 40. Cleat 60 is preferred considering the ease of installing surgical cable 100 therewith.

In FIG. 3 second surgical loop 112 is shown installed on vertebrae 104 and 106 with crimp 122. For many procedures such as installing two surgical cables on selected vertebrae, it is preferable to alternately tighten and loosen the surgical loops until the vertebrae are positioned as desired. A separate cable tensioner 20 may be used with each surgical loop 102 and 112 to alternately increase and decrease the tension in the respective surgical loops.

Pawl 48 normally prevents second handle 40 from sliding longitudinally away from first handle 30. By manually depressing pawl 48 into recess 50, pawl 48 is released from engagement with the adjacent portion of elongated shaft 22. When the surgeon depresses pawl 48, second handle 40 may slide longitudinally away from first handle 30 to release the tension in surgical cable 100. Thus, if separate cable tensioners 20 are attached to each surgical loop 102 and 112, respectively, the surgeon may alternately tighten and release the tension in the surgical loops 102 and 112 by alternatively squeezing and releasing the respective second handle 40.

This feature of the present invention allows the surgeon to provide the optimum tension in the loops on vertebrae 104 and 106. The ability of tensioner 20 to either increase or decease the tension in the surgical loops allows obtaining the optimum forces on the portion of the patient's body which will be secured by the surgical cables. This procedure is similar in many respects to tightening and loosening fasteners which are used to hold mechanical components together. After the desired amount of tension has been placed in loops 102 and 112, their respective crimps 120 and 122 may be compressed on the respective surgical cables 100 to trap the tension. A portion of crimps 120 and 122 and their respective surgical cables 100 may then be cut to allow removal of tensioners 20 and the remainder of surgical cables 100.

Cable tensioner 220 incorporating an alternative embodiment of the present invention is shown in FIGS. 4 and 5. Cable tensioner 220 is preferably used with a surgical cable and a crimp to trap the desired amount of tension in a loop formed by the surgical cable and crimp. As explained for cable tensioner 20, cable tensioner 220 may be used with surgical cable 100 and crimp 120 to tighten first loop 102 around a selected portion of a patient's body and to trap the desired amount of tension within first loop 102.

Cable tensioner 220 has three main components, elongated shaft 222, first handle 230 and second handle 240. An important feature of this embodiment of the present invention is that the main components of cable tensioner 220 may be formed from aluminum or other suitable metals and composite materials which are appropriate for sterilization and repeated surgical use.

First handle 230 is preferably secured to one end of elongated shaft 222. First handle 230 is generally configured to fit within the palm of a surgeon's hand (not shown). Elongated shaft 222 and first handle 230 cooperate to form a generally "T" shaped surgical tool.

Second handle 240 is slidably disposed on the exterior of elongated shaft 222 intermediate the ends thereof. Elongated shaft 222 has a generally circular cross section. First slot 224 is formed in the exterior of elongated shaft 222 intermediate the ends thereof. A plurality of serrations 225 are provided within slot 224. Second handle 240 includes opening 242 which is sized to fit over the portion of elongated shaft 222 containing first slot 224. Opening 242 cooperates with the exterior of elongated shaft 222 to allow second handle 240 to slide longitudinally over the exterior of elongated shaft 222.

The other end 226 of elongated shaft 222 has an opening 228 which provides a portion of the means for releasably securing a portion of a surgical cable with end 226 of elongated shaft 222. A second slot 229 is provided in the exterior of elongated shaft 222 extending from end 226. As explained for second slot 29 of cable tensioner 20, slot 229 is provided to assist with attachment of a surgical cable to second handle 240.

Second handle 240 and elongated shaft 222 also have a generally "T" shaped configuration. Second handle 240 preferably includes extensions 244 and 246 which are provided for engagement by the fingers of a surgeon's hand. Cable tensioner 220 is generally used by resting first, fixed handle 230 against the palm of a surgeon's hands and engaging extensions 244 and 246 by the fingers of the surgeon's hand. When the surgeon squeezes his fingers, second handle 240 will slide longitudinally towards first, fixed handle 230.

Second handle 240 includes pawl 48 disposed within recess 50 of extension 244. Pin 52 is provided to secure pawl 48 within recess 50 and to allow pawl 48 to pivot with respect to pin 52 and the exterior of elongated shaft 222 adjacent thereto. First spring 54 is disposed within recess 50 and contacts a portion of pawl 48. Spring 54 cooperates with pivot pin 52 to bias pawl 48 to contact the exterior of elongated shaft 222 adjacent thereto.

Pawl 48 is preferably sized to fit within longitudinal slot 224 and to engage serration 225 therein. Pawl 48 cooperates with first longitudinal slot 224 to prevent rotation of second handle 240 relative to spring 54 and pivot pin 52 cooperate with pawl 48 to allow longitudinal movement of second handle 240 towards first handle 230. In a similar manner spring 54, pivot pin 52 and pawl 48 cooperate with each other and serration 225 to prevent undesired movement of second handle 240 in the direction away from first handle 230. As previously discussed for cable tensioner 20, pawl 48 allows controlled movement of second handle 240 to tighten and loosen tension in a surgical cable attached to cable tensioner 220.

Second handle 240 includes cleat 60 which is attached to the exterior of second handle 240 by pivot pin 62. Since second handle 240 is preferably formed from metal, plate 64 used with tensioner 20 is not required. Torsion spring (not shown, but identical to torsion spring 66 of FIG. 2) is provided to bias cleat 60 into contact with shoulder 241 formed on second handle 240. Cleat 60 cooperates with shoulder 241 on second handle 220 to trap a portion of surgical cable 100 therebetween.

Cable tensioner 220 may be used with surgical cable 100 to secure first loop 102 with selected portions of a patient's body such as vertebrae 104 and 106. Crimp 102 is preferably secured to one end of surgical cable 100 and loop 102 placed around the selected portion of the patent's body. Crimp 120 and the attached end of surgical cable 100 are then secured to the other end 226 of elongated shaft 222 opposite from first handle 230. A portion of surgical cable 100 is placed within second longitudinal slot 229 in the exterior of elongated shaft 222. Second slot 229 in elongated shaft 22 aligns surgical cable 100 with elongated shaft 222 and assists with engagement of a portion of surgical cable 100 with cleat 60.

One of the differences between cable tensioner 220 and cable tensioner 20 includes providing gauge 250, which indicates the amount of force applied to second handle 240 after a surgical cable has been secured to cable tensioner 220. The force measured by gauge 250 is an approximation of the tension applied to the surgical cable.

Elongated shaft 222 comprises first portion 222a attached to first handle 230 and second portion 222b, which is slidably disposed within first portion 222a. As shown in FIG. 5, second portion 222b of elongated shaft 222 preferably includes longitudinal passageway 236 extending partially therethrough. Alignment rod 232 is preferably attached to first portion 222a and extends from first handle 230 into longitudinal passageway 236. Biasing means or spring 234 is preferably disposed on the exterior of alignment rod 232 between first portion 222a and second portion 222b.

When one portion of a surgical cable is attached to end 226 of elongated shaft 222 and another portion of the surgical cable is attached to second handle 240, movement of second handle 240 towards first handle 230 will result in longitudinal movement of second portion 222b relative to first portion 222a and compression of spring 234. Movement of second handle 240 towards first handle 230 will thus result in movement of gauge 250 relative to scale 252. The amount of force required to move second handle 240 towards first handle 230 is proportional to the spring constant of biasing means 234. Therefore, the position of gauge 250 on scale 252 is an indication of the force being applied to second handle 240 and to the surgical cable attached to tensioner 220. Thus, cable tensioner 220 with gauge 250 provides an indication of the amount of tension being applied to a surgical loop around a selected portion of the patient's body.

Scale 252 may be used to indicate increments of force such as 20, 40, 60 and 80 pounds. Pawl 48 cooperates with second handle 240 to trap the desired amount of tension within the attached surgical cable as indicated by gauge 250.

An important feature of cable tensioner 220 is that spring 234 is located between second handle 240 and first handle 230 contained within second portion 222b of elongated shaft 222. This position for spring 234 minimizes potential adverse consequences from a failure of spring 234 and associated components.

Cable tensioner 20 and 220 may be used with various types of surgical cable crimps, clamps and locks. Cable tensioners 20 and 220 are not limited to use with crimp 120. Also, if cable tensioners 20 and 220 are used with self-locking crimps, pawls 48 may not be required for use with second handles 40 and 240 to hold the desired amount of tension in the surgical cable loop.

Although the present invention and its advantages have been described in detail, it should be understood that various changes, substitutions and alterations can be made without departing from the spirit and the scope of the invention as defined by the following claims.

What is claimed is:

1. Apparatus for installing a surgical cable to selected portions of a patient's body comprising:
   an elongated shaft having a first handle secured to a first end of the shaft;
   a second handle slidably disposed on the shaft intermediate the first and a second end thereof;
   means for releasably securing a portion of the surgical cable adjacent the second end of the shaft opposite from the first handle;
   means for securing another portion of the surgical cable to the second handle;
   the second handle having an opening sized to allow the second handle to slide longitudinally over the exterior of the elongated shaft; and
   means for selectably preventing longitudinal movement of the second handle in one direction.

2. The apparatus as defined in claim 1 wherein the means for securing a portion of the surgical cable to the second handle further comprises a cleat pivotally attached to the second handle and a spring biasing the cleat to engage the portion of the surgical cable.

3. The apparatus as defined in claim 1 further comprising:
   the second end of the elongated shaft having an opening to receive a crimp carried by the surgical cable; and
   a longitudinal slot extending partially through the elongated shaft to allow disposing a portion of the surgical cable within the longitudinal slot to assist attachment to the second handle.

4. The apparatus as defined in claim 1 wherein the means for selectably preventing longitudinal movement of the second handle comprises a pawl for releasably engaging the exterior of the elongated shaft to prevent longitudinal movement of the second handle in one direction away from the first handle.

5. The apparatus as defined in claim 1 further comprising the elongated shaft having a generally circular cross section with an opening in the second handle to allow the second handle to be slidably disposed on the exterior of the elongated shaft.

6. Apparatus for installing a surgical cable to selected portions of a patient's body comprising:
   an elongated shaft having a first handle secured to a first end of the shaft;
   a second handle slidably disposed on the shaft intermediate the first and a second end thereof;
   means for releasably securing a portion of the surgical cable adjacent the second end of the shaft opposite from the first handle;
   means for securing another portion of the surgical cable to the second handle; and
   wherein the elongated shaft comprises:
   a first portion attached to the first handle
   a second portion slidably connected to the first portion and
   means for biasing the second portion to extend from the first portion.

7. The apparatus as defined in claim 6 wherein the biasing means comprises a spring which responds to force applied to the second portion of the elongated shaft by the second handle.

8. The method of attaching a surgical cable to a selected portion of a patient's body comprising the steps of:
   providing a first surgical cable having a crimp secured to one end thereof;
   forming a portion of the first surgical cable into a first loop around a selected portion of the patient's body;
   slidably disposing the other end of the first surgical cable through the crimp;
   providing a first cable tensioner having a first end and a handle slidably disposed on the exterior of the first end, the
   engaging the crimp of the first loop with the first end of the first cable tensioner;
   attaching an intermediate portion of the first surgical cable to the handle;
   sliding the handle longitudinally to place the desired amount of tension within the first loop; and
   compressing the crimp to trap the desired amount of tension within the first loop.

9. Apparatus for installing a surgical cable with selected vertebrae of a patient's spine comprising:
   an elongated shaft having a first handle fixed to a first end of the shaft;

a second handle slidably disposed on the exterior of the shaft intermediate the first end and a second end thereof;

means for releasably securing a portion of the surgical cable adjacent to the second end of the shaft opposite from the first handle;

means for securing another portion of the surgical cable to the second handle; and means for allowing movement of the second handle towards the first handle and restricting movement of the second handle away from the first handle.

10. The apparatus as defined in claim 9 further comprising:

the second handle having an opening sized to allow the second handle to slide longitudinally over the exterior of the elongated shaft; and a pawl partially disposed within a recess in the second handle to provide a portion of the means for restricting movement of the second handle.

11. The apparatus as defined in claim 9 further comprising: the second end of the elongated shaft having an opening to receive a crimp carried by the surgical cable; and a longitudinal slot extending partially through the elongated shaft to allow disposing a portion of the surgical cable within the longitudinal slot to assist attachment to the second handle.

12. The apparatus as defined in claim 9 further comprising a pawl for releasably engaging the exterior of the elongated shaft to prevent longitudinal movement of the second handle in the direction away from the first handle and for allowing movement of the second handle in the direction towards the first handle.

13. The apparatus as defined in claim 9 further comprising the elongated shaft having a generally circular cross section with an opening in the second handle to allow the second handle to be slidably disposed on the exterior of the elongated shaft.

14. The apparatus as defined in claim 9 wherein the elongated shaft further comprises:

a first portion attached to the first handle;

a second portion slidably connected to the first portion; and means for biasing the second portion to extend longitudinally from the first portion.

15. The apparatus as defined in claim 14 wherein the biasing means comprises a compression spring which responds to force applied to the second portion of the elongated shaft by the second handle after the surgical cable has been attached to both the other end of the elongated shaft and the second handle.

16. The apparatus as defined in claim 9 wherein the means for securing a portion of the surgical cable to the second handle further comprises a cleat pivotally attached to the second handle and a spring biasing the cleat to engage the portion of the surgical cable.

17. A method of attaching surgical cables to selected portions of a patient's body comprising the steps of:

forming a portion of a first surgical cable into a first loop around a selected portion of the patient's body;

engaging one end of the first loop with a first end of a first cable tensioner;

attaching another portion of the first surgical cable to a handle slidably disposed on the exterior of the first cable tensioner;

sliding the handle longitudinally to place the desired amount of tension within the first loop;

forming a portion of a second surgical cable into a second loop around another selected portion of the patient's body;

engaging one end of the second loop with a first end of a second cable tensioner;

attaching another portion of the second surgical cable to a handle slidably disposed on the exterior of the second cable tensioner;

Sliding the handle longitudinally to place the desired amount of tension within the second loop;

forming the second loop with a crimp secured to one end of the second surgical cable and the second surgical cable slidably disposed through the crimp; and compressing the crimp to trap the desired amount of tension within the second loop.

* * * * *